US007862526B1

(12) United States Patent
Skowron et al.

(10) Patent No.: US 7,862,526 B1
(45) Date of Patent: Jan. 4, 2011

(54) CERVICAL TRACTION ASSEMBLY WITH SENSORY FEEDBACK

(76) Inventors: John Skowron, 324 Rosehaven Dr., Raleigh, NC (US) 27609; John Fedorjaka, 408 Maple Creek Ct., Apex, NC (US) 27502; Steve Smith, 108 Pinecroft Dr., Raleigh, NC (US) 27609

( * ) Notice: Subject to any disclaimer, the term of this patent is extended or adjusted under 35 U.S.C. 154(b) by 263 days.

(21) Appl. No.: 12/185,521

(22) Filed: Aug. 4, 2008

(51) Int. Cl.
*A61F 5/00* (2006.01)

(52) U.S. Cl. .......... 602/18

(58) Field of Classification Search .......... 602/32-39, 602/18; 128/DIG. 23
See application file for complete search history.

(56) References Cited

U.S. PATENT DOCUMENTS 3,871,366 A * 3/1975 Cotrel .......... 602/33
4,407,274 A * 10/1983 Goodley .......... 606/241
4,580,554 A * 4/1986 Goodley .......... 606/201
6,113,563 A * 9/2000 D'Amico et al. .......... 602/32

* cited by examiner

*Primary Examiner*—Michael A. Brown
(74) *Attorney, Agent, or Firm*—Ishman Law Firm P.C.

(57) ABSTRACT

A cervical traction assembly whereby the user can exert a variable load on the cervical spine and receive a sensory feedback when the traction is at or within range of a target load. The assembly includes a head harness wrapped around the forehead of the user that is attached to a traction bar connected to a load line assembly that passes through a direction reversal pulley and terminates with force straps actuated by the user's legs. The load line assembly includes a spring force scale that includes a control assembly that allows the user to set a target applied load and receive sensory feedback in the form of varying audible signals as the user applied load approaches, meets and exceeds a target load range.

6 Claims, 10 Drawing Sheets

CERVICAL TRACTION ASSEMBLY WITH SENSORY FEEDBACK

FIELD OF THE INVENTION

The present invention relates to devices for applying cervical traction, and, in particular, to a cervical traction device wherein the user selects and applies a loading to the cervical area and receives audible feedback with respect thereto.

BACKGROUND OF THE INVENTION

Cervical traction devices are used for applying traction to the cervical spine. At a practitioner's office elaborate and expensive devices are available. While beneficial under the operation of skilled personnel, these units are normally too complex and expensive for home use where it is recognized that therapeutic value is obtained through the regular use in accordance with prescribed protocols.

Many such devices have been available and generally rely on static weights applied at a harness wrapped around the user's head. It is also recognized that the use of intermittent and variable loadings provides additional advantages. One such traction device is disclosed in U.S. Pat. No. 4,407,274 to Goodly wherein a variable loading is applied by foot extension by the user with the loading displayed for viewing and control by the user. While providing versatility in loading, certain deficiencies are apparent. The load is displayed on a spring loaded scale requiring the user to adjust body position for viewing, thereby redirecting user focus from the routine. Further, the load lines can twist the scale during use preventing the user from monitoring the loading. Additionally, the scale load units are tightly spaced, making it is difficult for a user to maintain an observable constant loading. It would accordingly be desirable to provide a home use cervical traction device that would enable the user to undertake verifiable traction protocols without the limitations of the above approaches.

SUMMARY OF THE INVENTION

The present invention provides cervical traction assembly whereby the user can exert a variable load on the cervical spine and receive a sensory feedback when the traction is at or within range of a target load. The assembly includes a head harness wrapped around the forehead of the user that is attached to a traction bar connected to a load line assembly that passes through a direction reversal pulley and terminates with force straps actuated by the user's legs. The load line assembly includes a spring force scale that includes a control assembly that allows the user to set a target applied load and receive sensory feedback in the form of varying audible signals as the user applied load approaches, meets and exceeds a target load range.

In one aspect, the invention provides a cervical traction device for applying traction to the cervical spine of a user wherein a harness wraps about the head of a user and a pair of strap members is attached at one end to the harness and at the end to an elongated traction bar. A load line is attached at one end to said traction bar and through a load reversal device mounted on a support surface beyond the head of the user that routes load line from said traction bar to position over said user connected with a force and feedback assembly. A force loading member operable by the legs of the user connected to the other end of said force and feedback assembly for applying a force thereto. The force and feedback assembly is operative to provide a sensory output responsive to said force applied by said force loading member. In other aspects, the sensory output is audible; the force and feedback assembly may include a spring member operatively connected between said load line and said force loading member, and the sensory output is responsive to change in spring length from the force; the force and feedback assembly may include a battery power source connected to first circuit means and providing a first output related to said force on said spring, a microprocessor receiving said first output and actuating said sensory device to provide and audible output based on said force; a second circuit means may be connected to the power source and an indicator provided for setting a target load force and providing a second output related to said setting to the microprocessor that compares the first output and the second output and actuates the sensory device to produce an audible output characteristic of said comparing; the output characteristic may be based on an equivalence of said first output and said second output and another output characteristic provided based on a difference in said first output and said second output wherein a first output characteristic is based on said first output exceeding said second output and a second output characteristic is based on a second output exceeding said first output or the output characteristic based on the first output being within a predetermined range of the second output.

DESCRIPTION OF THE DRAWINGS

The above and other features and advantages of the present invention will become apparent upon reading the following description taken in conjunction with the accompanying drawings in which.

DESCRIPTION OF THE PREFERRED EMBODIMENTS

Figure 1:
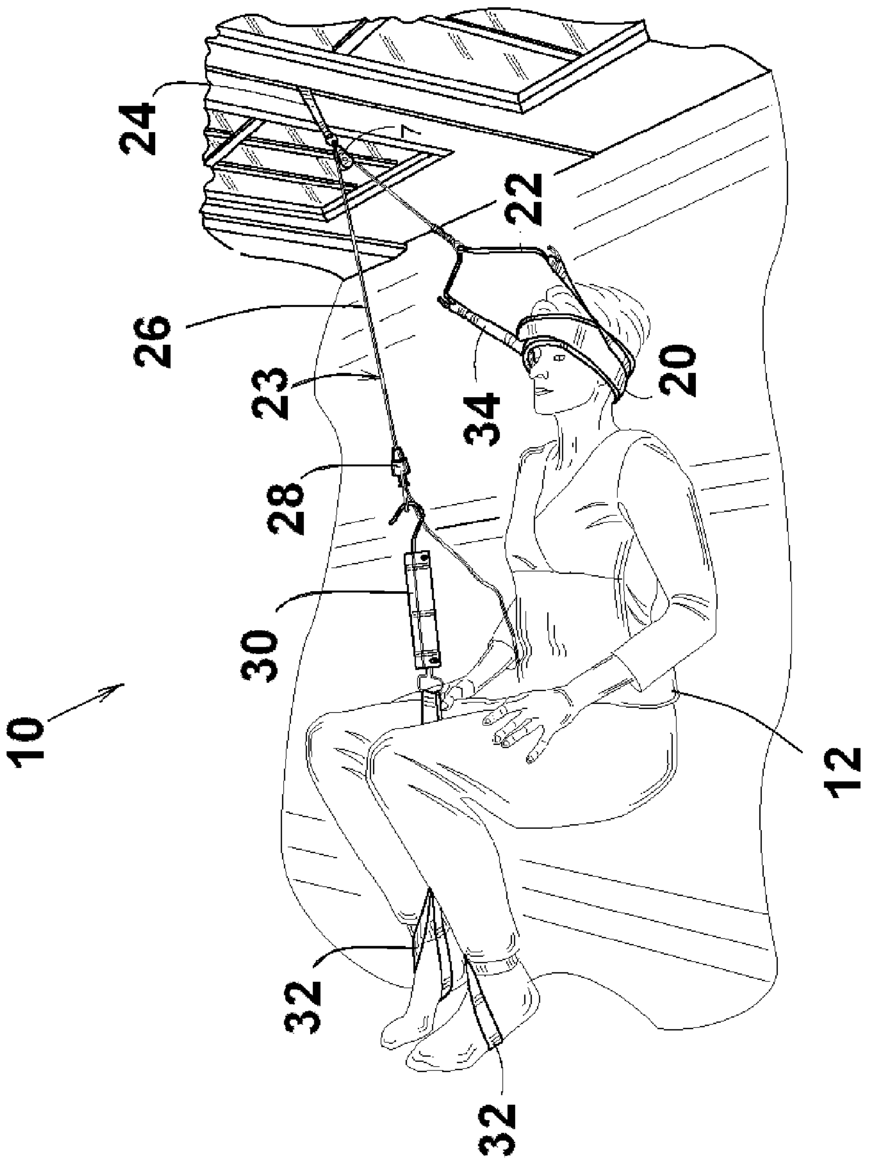
FIG. 1 is a perspective drawing of the cervical traction assembly in use.
Figure 2:
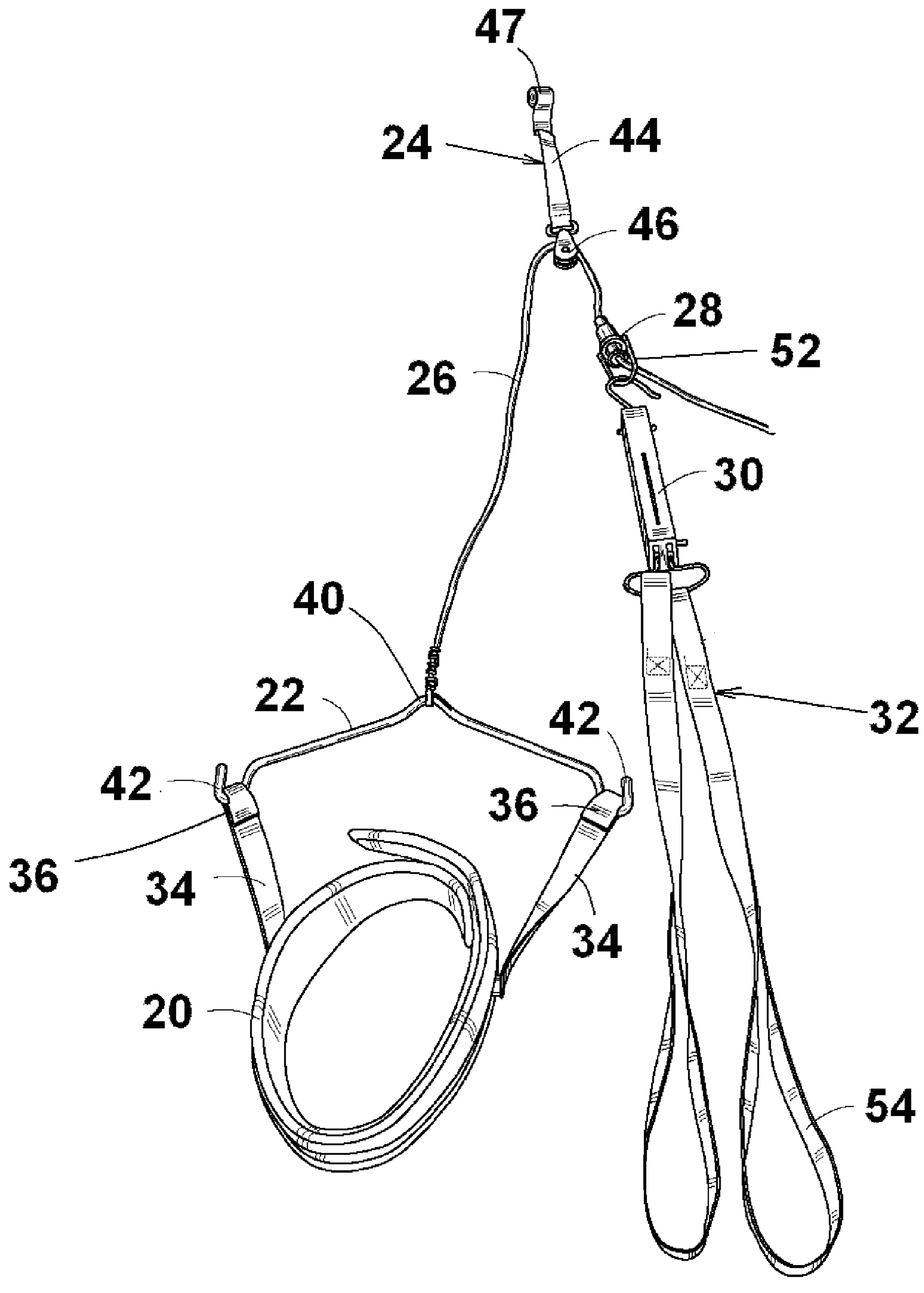
FIG. 2 is a perspective view of the components of the cervical traction assembly of FIG. 1.
Figure 3:
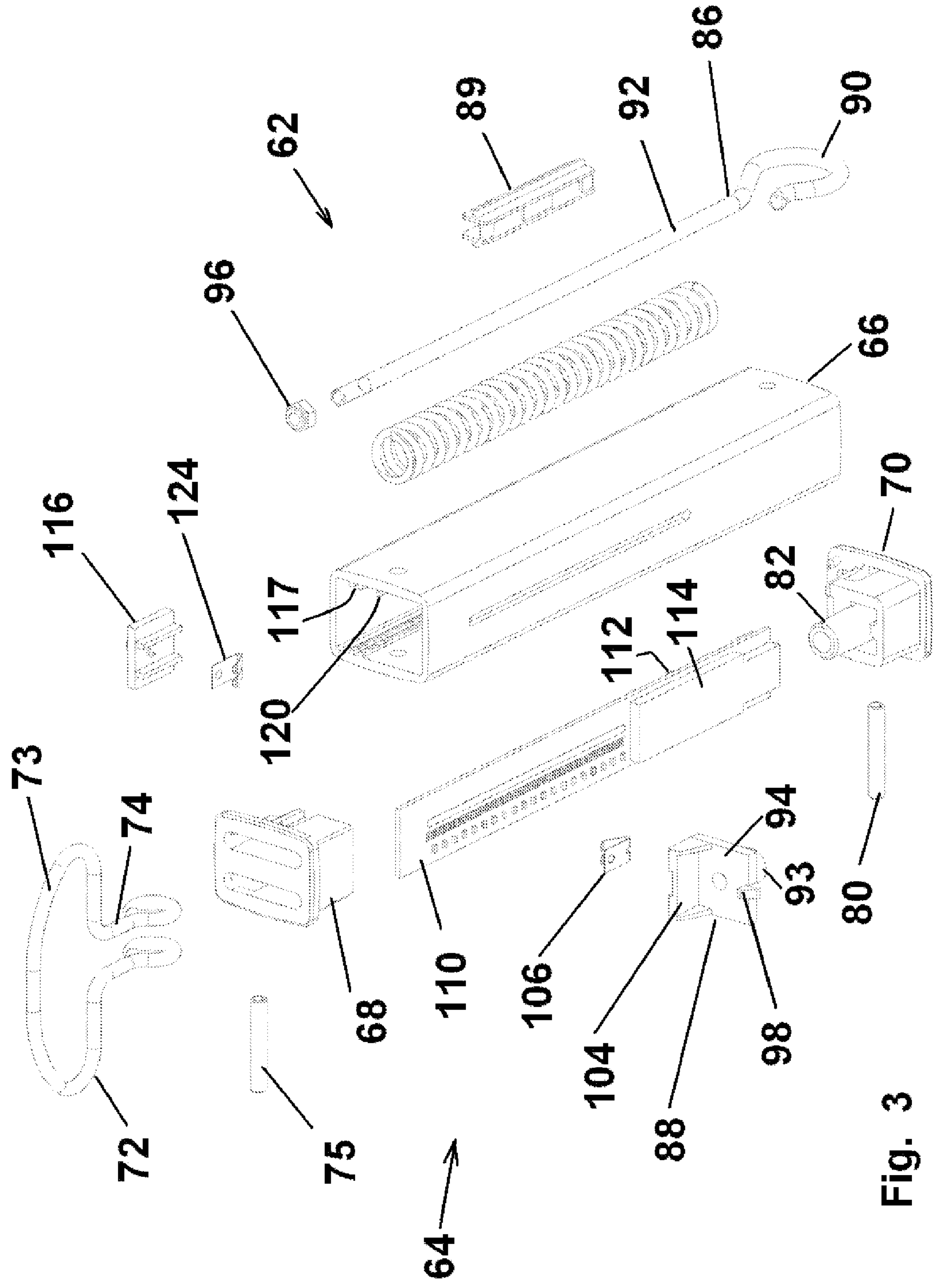
FIG. 3 is an exploded perspective view of the force scale.
Figure 4:
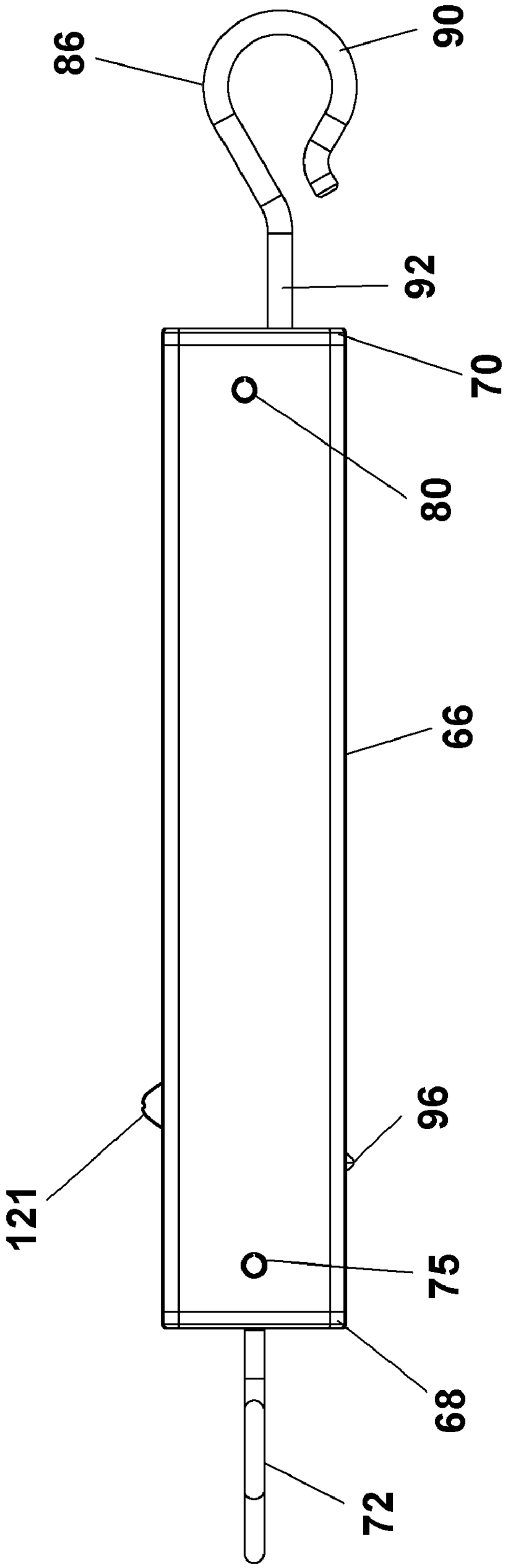
FIG. 4 is a side view of the force scale.
Figure 5:
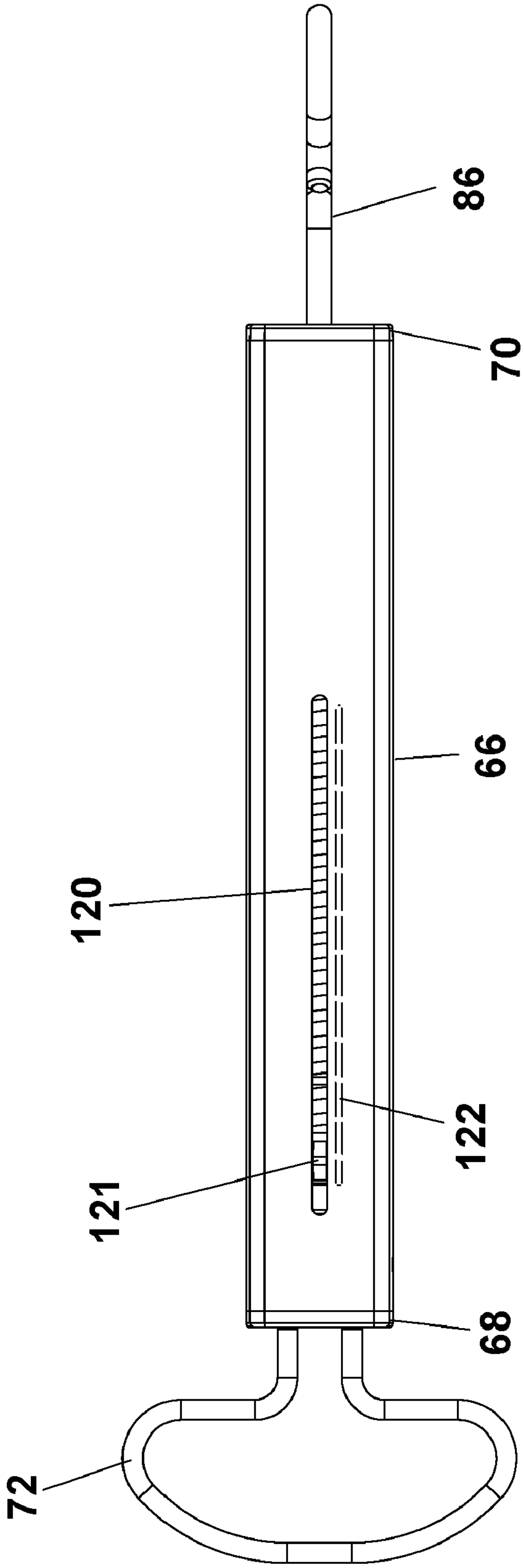
FIG. 5 is a top view of the force scale.
Figure 6:
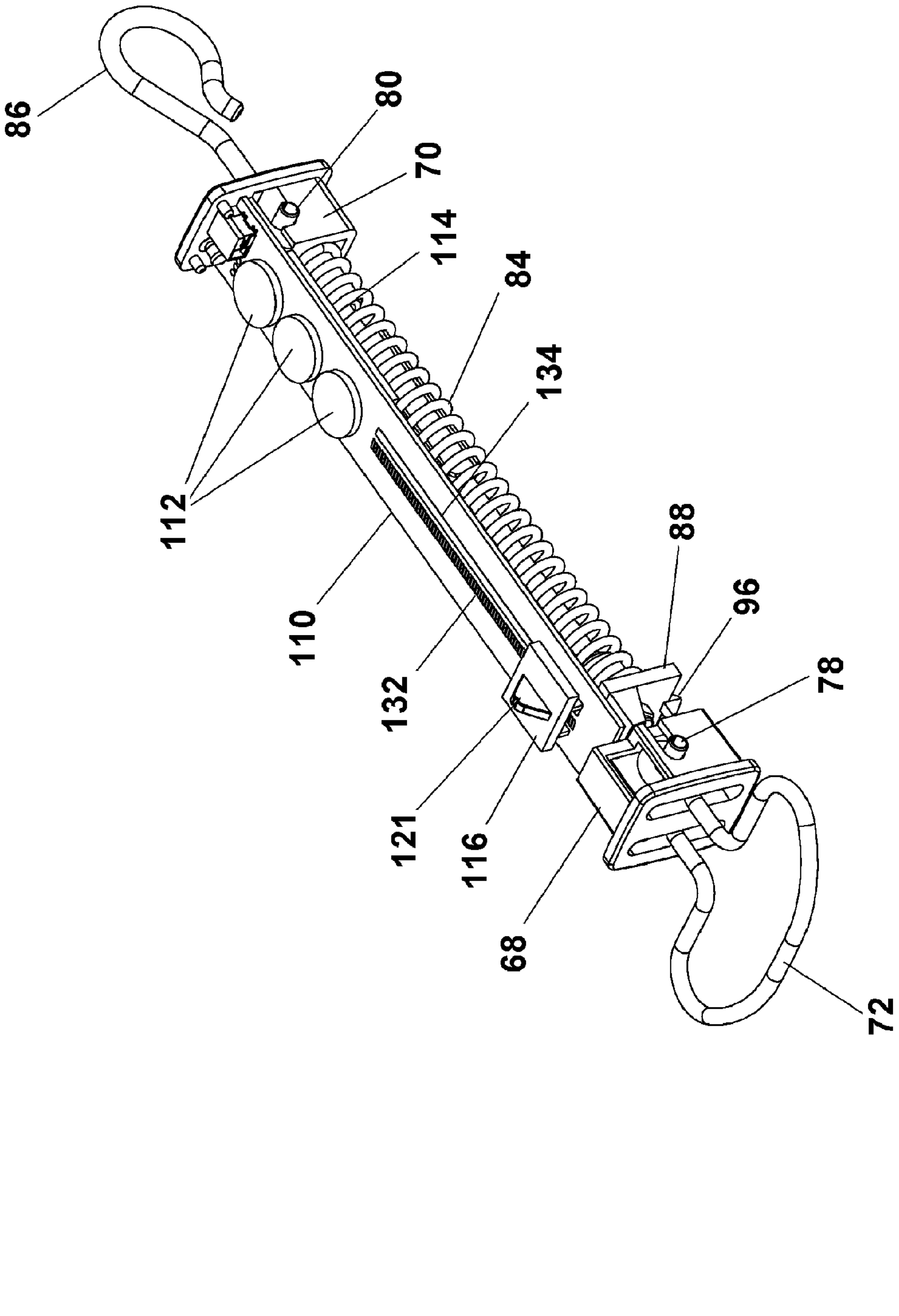
FIG. 6 is a perspective view of the force scale with the case removed.
Figure 7:
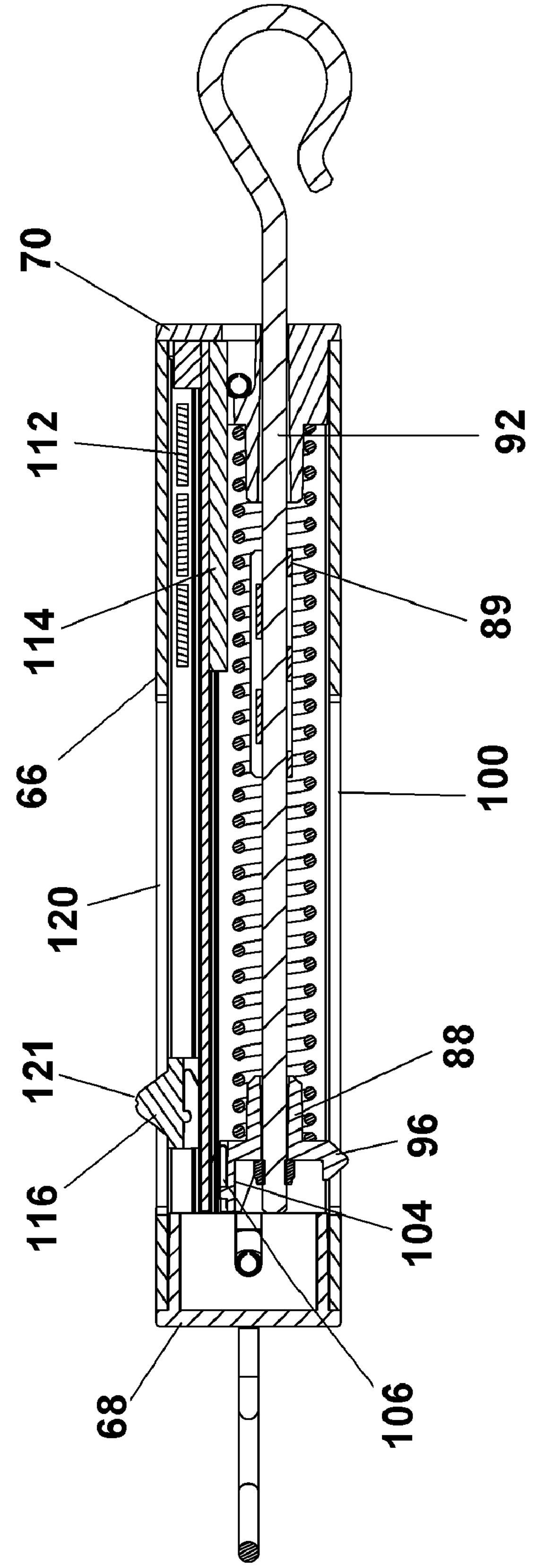
FIG. 7 is a side cross sectional view of the force scale.
Figure 8:
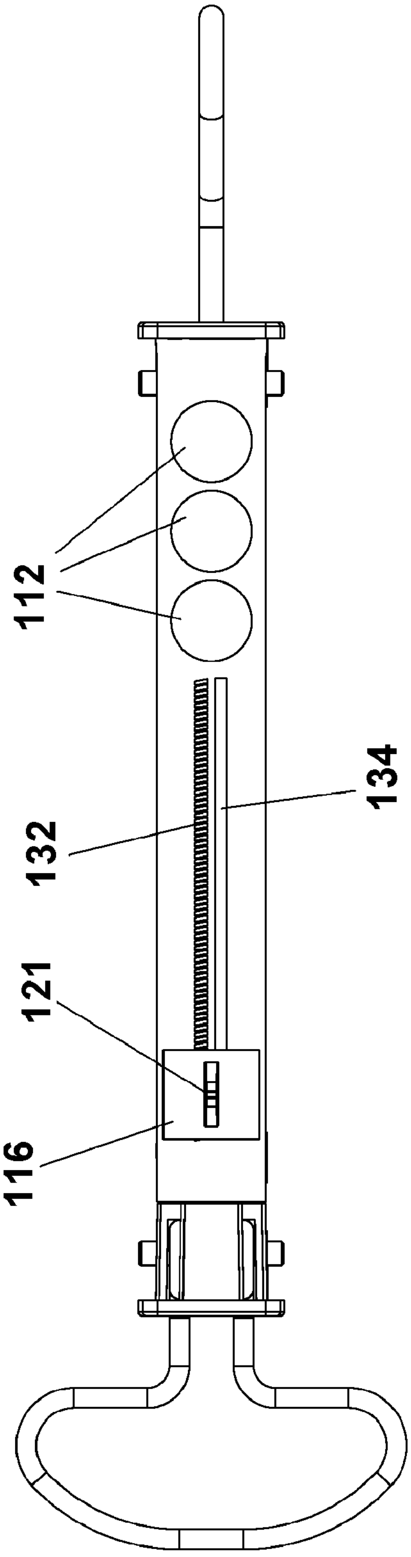
FIG. 8 is a top view of the force scale with the case removed.

Referring to FIGS. 1 and 2, there is shown a cervical traction assembly 10 whereby a user 12 can self apply a variable and quantifiable traction loading to the cervical spine in accordance with a prescribed protocol and receive sensory feedback as the loading approaches, reaches and exceeds a predetermined applied load range.

The cervical traction assembly 10 includes a harness 20 wrapped around the forehead of the user 12, a traction bar 22, and a load line assembly 23 including a mounting assembly 24, a load line 26, a line clamp 28, a force scale 30, and force straps 32.

The harness 20 is an elongated strap of a soft flexible material that is wrapped around the forehead of the user 12. The harness 20 has ends thereof attached by suitable fasteners such as hook and loop fastening systems. The harness 20 includes side straps 34 having distal end loops 36. The traction bar 22 is generally V-shaped having a pair of diverging side arms 38 integrally joined at an arcuate center section 40 and terminating with reversely turned ends 42. In assembly, the distal loops 36 are inserted into the ends 42 of the traction bar 22. The traction bar 22 is formed of a rigid material, such as metal or plastic. A steel rod of circular cross section is used in the present embodiment.

The mounting assembly 24 is adapted for mounting on a solid vertical surface. Herein, the mounting assembly 24 is adapted for retention in a door casing between the door and jam at an elective height for proper application of cervical traction force. The mounting assembly 24 includes a mounting strap 44 attached at one end to a suitable line reversing device in the form of a pulley 46 and having an enlarged terminal end 47 inserted behind the door for resisting separation or movement under loading.

The load line 26 is flexible line of suitable material such as braided rope. The load line 26 is attached at one end to the center section 40 of the traction bar 22 and extends to and around the pulley 46 with the other free end extending through the line clamp 28.

The line clamp 28 is a commercially available length adjustment device including a clamp body having a socket receiving an annular clamping ferrule through which the free end 48 of the load line 26 extends. The ferrule may be adjustably positioned along the line. Upon application of force the ferrule is compressively seated in the clamp body socket and about the line to maintain position thereon. The line clamp 28 accommodates the variables in user and mounting positions. The clamp body includes a pivotal bracket 52 that is releasably attached to one end of the force scale 30.

The force straps 32 are formed an elongated flexible material and include mounting loops 54 at one end attached to the force scale 30 and foot loops 56 at the other end for receipt of the user's feet for application of user imparted loading to the assembly for applying cervical traction. The length of the force straps 32 preferably places the force scale 30 at a mid torso position in use.

Referring to FIGS. 3 through 8, the force scale 30 interconnects the force straps 52 and the load line 26 and allows the use to set a traction load and to receive sensory feedback as the applied load is increased, met or exceeded. The force scale 30 comprises a case assembly internally housing a spring assembly 62 and a load set and feedback assembly 64. The case assembly includes an extruded aluminum rectangular tubular case 66 having a mount cap 68 at one end and a hook cap 70 at the other end. The mount cap 68 includes a base telescopically inserted into the end of the case and a pair of spaced slots at the head thereof receiving a mount bracket 72. The mount bracket 72 is provided with a closed hook end 73 and a pair of spaced arms 74 with eyelets. The arms 74 are inserted into slots in the mount cap 68 and secured thereto by a spring pin 75 extending through aligned holes in the mount cap base, the side walls of the case, and the eyelets whereby the mount bracket 72 is pivotally connected to the mount cap 68.

The hook cap 70 has a base inserted into the other end of the case and secured thereto by a spring pin 80 extending through aligned holes in the base and the side walls of the cane. The hook cap 70 includes a cylindrical rear sleeve 82. An actuator hole extends through the hook cap 70 including the sleeve.

The spring assembly 62 includes a coiled compression spring 84, and actuating arm 86, and an end guide 88. A spring retainer 89 is slidably housed in the spring 84 for preventing sagging thereof to thereby avoid with the feedback assembly 64. The spring 84 has one end inserted over the sleeve 82 in the hook cap 70 and the other end terminating adjacent the mount cap 68. The actuating arm 86 includes a curved end hook 90 connected to the bracket 52 and a cylindrical actuating shaft 92 extending through the actuator hole of the hook cap 70 and the compression spring 84. The shaft 92 has a terminal threaded end projecting beyond the end of the spring. The end guide 88 has a cylindrical mounting sleeve 93 received within the end of the spring and a through hole through which the end of the actuating arm projects. The end guide 88 includes a rectangular slide block 94 slidably supported at the inner side walls and base of the case and engaging the end of the spring. A threaded nut 96 is coupled to the threaded end of the shaft 90 and is adjusted to provide an initial preload on the spring. The slide block 94 includes a projecting tip 98 that extends through and rides within a longitudinal slot 100 from in the base wall of the case. The slot 100 includes scaled indicia 102 at the side thereof whereby the position of the tip 98 with respect thereto gives a reading of the operative applied loading on the force scale. The guide block includes a rearwardly projecting flange 104 carrying a double blade spring contact 106 for use in load measurement as described below.

The feedback assembly 64 includes a rectangular printed circuit board 110, a battery unit 112, a controller 114 and load set slide 116. The board 110 is telescopically longitudinally inserted into slots 117 (FIG. 3) formed on the interior side walls of the case 66. The case includes a top longitudinal slot 120 through which the indicating tip 121 of the load set slide projects allowing the slide to be variably position at target traction indicia 122 (FIG. 5) at the side thereof. The battery unit 112 comprises three batteries mounted on the top surface of the board and enclosed by a protective cover. The controller 114 is mounted on the bottom surface of the board 110 and enclosed by a protective cover. The target weight slide 116 includes a double blade spring contact 124 that engages and traverses the board circuitry in setting the target load for the feedback assembly. The spring contact 106 on applied weight slide engages the lower surface of the board and traverses the board circuitry in establishing and denoting the applied load by the user.

Figure 9:
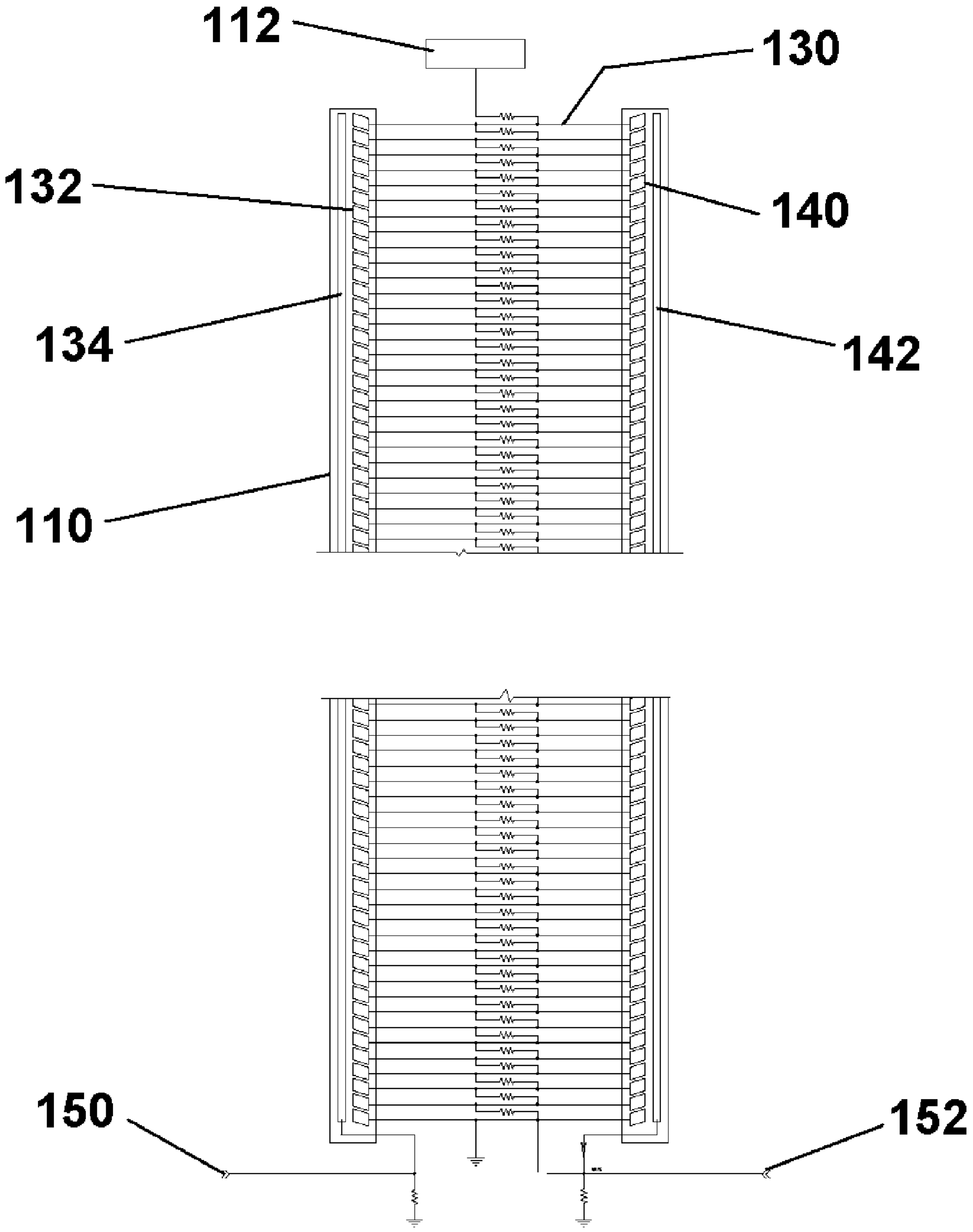
FIG. 9 is a schematic drawing of the circuit board for the force scale.

Referring to FIG. 9, the board 110 comprises an array of serially connected resistive circuits 130 connected to the battery unit 112. On the top surface of the board on the adjust side are a series of contact pads 132 connected to an opposed resistive circuit 130 and a continuous conductive strip 134 is spaced outwardly thereof. In operation, one blade of the contact 124 successively engages the pads 132 and the other blade traverses the strip 134. On the bottom surface on the applied load side are a similar series of contact pads 140 connected to an opposed circuit at vias, not shown, and a continuous conductive strip 142. Both surfaces are shown in a common plane for convenience of illustration. In operation, one blade of the applied load contact 106 successively engages the pads 140 and the other blade continuously engages the strip 142. The target load side is outputted from strip 134 at output 150. The applied load side is outputted from strip 142 at output 152. The board thus functions as dual potentiometers producing an output related to position, and correlating to a loading either as set or applied.

Figure 10:
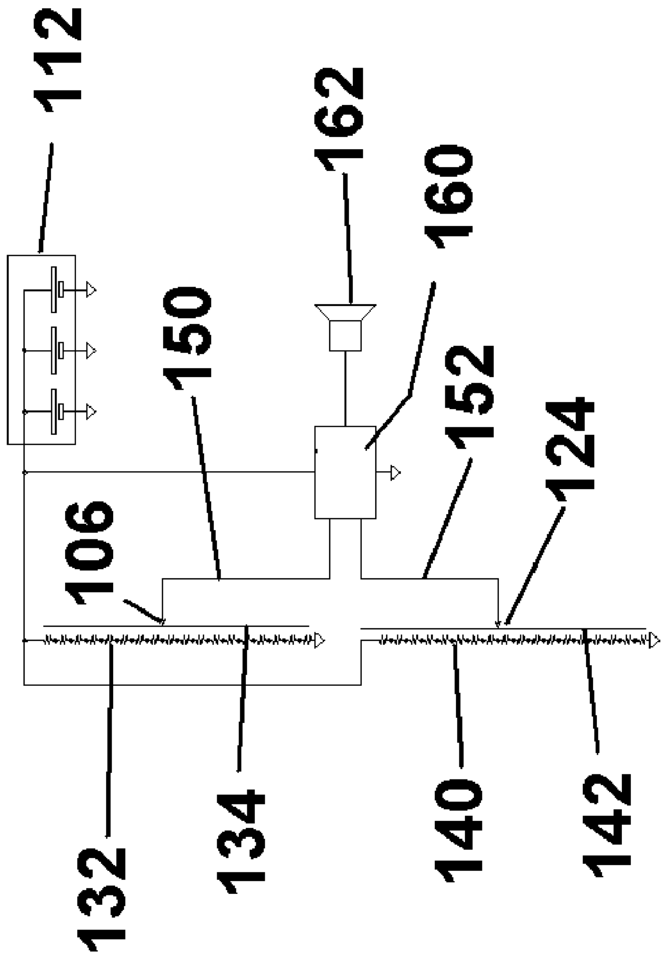
FIG. 10 is a schematic drawing of the controller for the force scale.

Referring to FIG. 10, the outputs 150, 152 are fed to a microcontroller 160. The microcontroller 160 processes the outputs and provides a signal to a sensory audio device 162, such as a piezoelectric beeper.

The microcontroller) 40 is programmed to compare the outputs and produce a response at the device 162 indicative of the proximity of the applied load to the target load. A suitable microcontroller is an 8-pin Flash-based 8-bit CMOS microcontroller available as product 12F675 from Microchip. In the present embodiment, the microcontroller may provide for a first type response at one level when the applied load is above or below the target load, and a second type or silence when the loads are equal. Different responses may be used to distinguish the above target loads from the below target loads. Further and preferred, a tolerance range is provided for the target load taking into consideration that it is extremely difficult for the user to achieve and maintain an exact loading. Therein, a first frequency is applied when the applied load is less than the lower limit of the target load, the same or a differing frequency when the applied load is greater than the upper limit of the target load, and a still differing response when the range is achieved. In the preferred embodiment a single beep is used for the lower loads, silence for the target range, and a double beep for the higher loads. It will be appreciated that other type of auditory distinction may be used.

For use, the assembly is mounted as shown in FIG. 1 and will vary from user to user and from one session to the next dependent on body position. For all installations it is preferred to mount the pulley at location that will provide a shallow traction angle of about 30° or less, and clearance of the return run to the load scale comfortably above the user's body. Also it is preferred to adjust the load line 26 at the line clamp 29 to locate the load scale 30 below the torso so that upon release it clears the user's head. The unloaded position should provide for sufficient flexure of the legs to effect a travel producing the desired applied load within the user's capability. The user sets the load slide at the target loading and then undertakes the desired protocol for applying traction. As the load increases, the user will receive auditory feedback from the sensory device at a response denoting loading below the target range. As the load increases to the target range, the response will change as programmed. Depending on the protocol, the user may seek to achieve this target range for a set period of time or comfort. The time may be monitored as desired, and could optionally be incorporated into the force scale. During the session, if the load exceeds the target range the user will receive feedback in the form of the indicative auditory response and can lower the loading to return to the target range. During the session, the feed back is supplied passively. At completion, the unit can be readily disassembled and compactly stored awaiting the next session.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the spirit and scope of the present invention. The disclosures and description herein are intended to be illustrative and are not in any sense limiting of the invention, which is defined solely in accordance with the following claims.

What is claimed:

1. A cervical traction device for applying traction to the cervical spine of a user, said traction device comprising:

a harness for wrapping about the head of a user;

a pair of strap members, each attached at one end to said harness;

an elongated traction bar, wherein the other ends of said strap members are attached to said traction bar;

a load line attached at one end to said traction bar;

a load reversal device for mounting on a support surface beyond the head of the user, said load reversal device routing said load line from said traction bar to position over said user;

a force and feedback assembly connected at one end to said load line;

force loading member operable by the legs of the user connected to the other end of said force and feedback assembly for applying a force thereto, said force and feedback assembly being operative to provide an audible sensory output responsive to said force applied by said force loading member and including a coiled compressing spring operatively connected between said lead line and said force loading member and wherein said sensory output is responsive to change in spring length from said force, said force and feedback assembly further including a battery power source connected to first circuit means and providing a first output related to said force on said spring, and a microprocessor receiving said first output and actuating said sensory device to provide an audible output based on said force.

2. The cervical traction device as recited in claim 1 including second circuit means connected to said power source, an indicator for setting a target load force and providing a second output related to said setting to said microprocessor, and said microprocessor comparing said first output and said second output and actuating said sensory device to produce a first audible output characteristic of said comparing.

3. The cervical traction device as recited in claim 2 wherein said first audible output characteristic is based on an equivalence of said first output and said second output.

4. The cervical traction device as recited in claim 3 wherein a second audible output characteristic is based on a difference in said first output and said second output.

5. The cervical traction device as recited in claim 3 wherein a third output characteristic is based on said first output being within a predetermined range of said second output.

6. The cervical traction device as recited in claim 2 wherein said first output characteristic is based on said first output exceeding said second output and said second output characteristic is based on said second output exceeding said first output.

* * * * *